(12) United States Patent
Wilson

(10) Patent No.: US 6,820,779 B1
(45) Date of Patent: Nov. 23, 2004

(54) PROSTHESIS DRESSING AID

(76) Inventor: Susann T. Wilson, 2601 Arbor Glen Dr., Bldg. 6-105, Twins Burg, OH (US) 44087

(*) Notice: Subject to any disclaimer, the term of this patent is extended or adjusted under 35 U.S.C. 154(b) by 0 days.

(21) Appl. No.: 10/440,535

(22) Filed: May 19, 2003

(51) Int. Cl.[7] .............................................. A47G 25/80
(52) U.S. Cl. ...................................................... 223/111
(58) Field of Search ................................ 223/111, 112, 223/118, 119; 383/207, 208, 209

(56) References Cited

U.S. PATENT DOCUMENTS

| 397,752 | A | * | 2/1889 | Ready .......................... 223/111 |
| 3,860,156 | A | | 1/1975 | Lawrence |
| 4,638,932 | A | | 1/1987 | Keller |
| 4,651,909 | A | | 3/1987 | Banting |
| 5,687,889 | A | | 11/1997 | Liden |
| 5,741,569 | A | | 4/1998 | Votino et al. |
| D407,186 | S | | 3/1999 | Koskela |
| 6,032,839 | A | * | 3/2000 | Joosten et al. .............. 223/112 |

* cited by examiner

Primary Examiner—John J. Calvert
Assistant Examiner—James Smith

(57) ABSTRACT

A prosthesis dressing aid for allowing a user to easily slip an article of clothing about the artificial limb. The prosthesis dressing aid includes a prosthesis being adapted to be attached to a user's limb; and also includes a sleeve being removably disposed about the prosthesis to facilitating dressing of the prosthesis with an article of clothing.

6 Claims, 2 Drawing Sheets

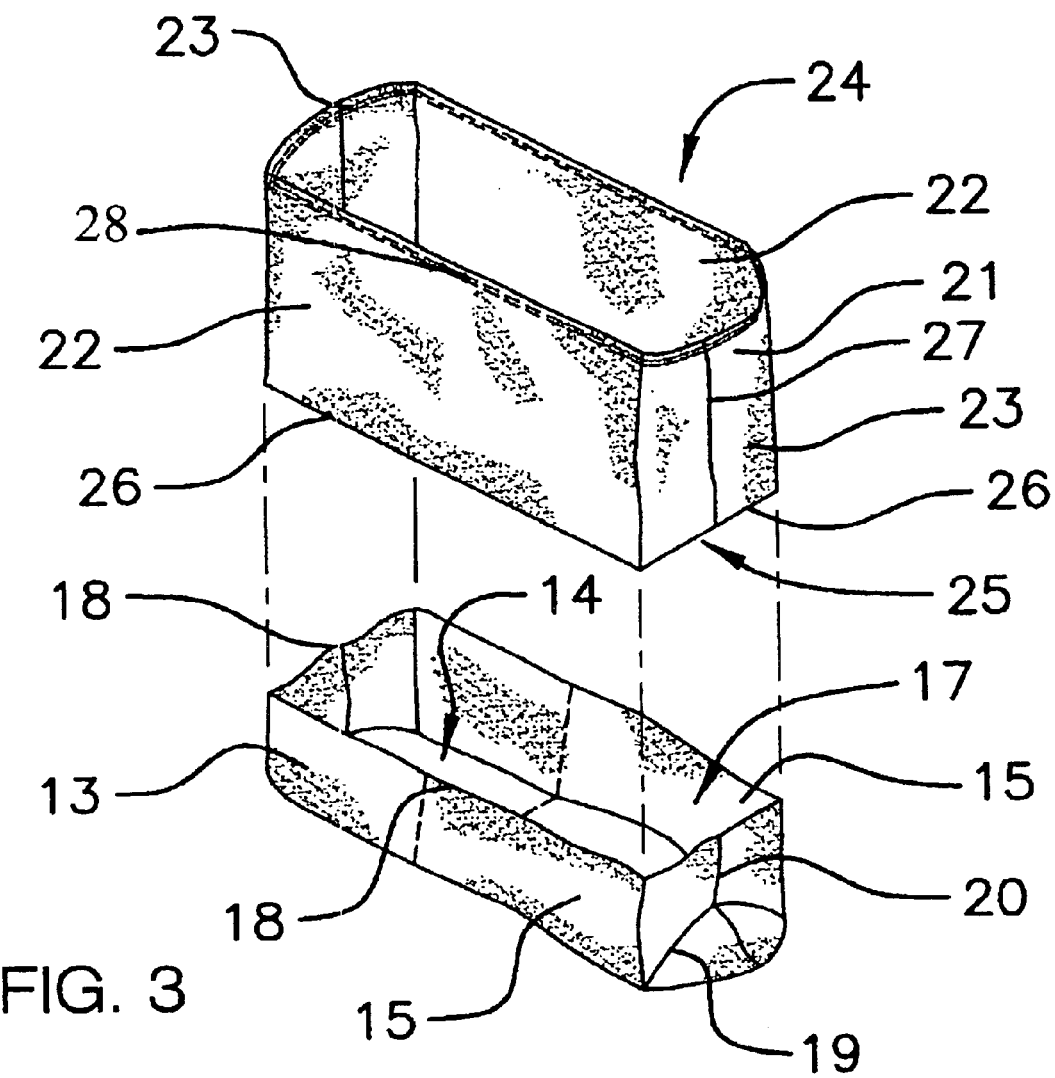
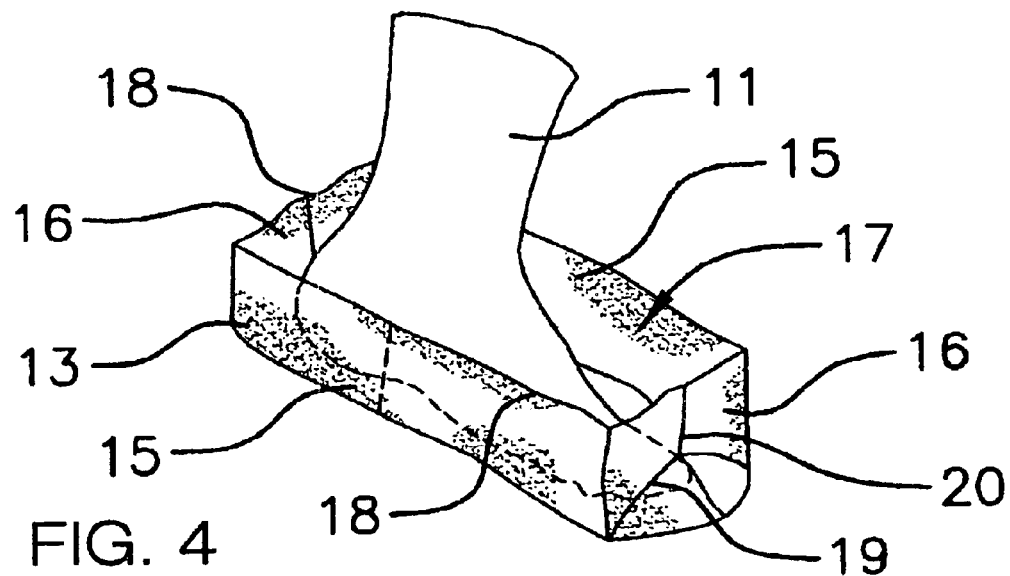

US 6,820,779 B1

PROSTHESIS DRESSING AID

BACKGROUND OF THE INVENTION

1. Field of the Invention

The present invention relates to prosthesis dressing aids and more particularly pertains to a new prosthesis dressing aid for allowing a user to easily slip an article of clothing about the artificial limb.

2. Description of the Prior Art

The use of prosthesis dressing aids is known in the prior art. More specifically, prosthesis dressing aids heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,741,569; U.S. Pat. No. 4,651,909; U.S. Pat. No. 4,638,932; U.S. Pat. No. 5,687,889; U.S. Pat. No. 3,860,156; and U.S. Pat. No. Des. 407,186.

While these devices fulfill their respective, particular objectives and requirements, the aforementioned patents do not disclose a new prosthesis dressing aid. The prior art includes tools and sheets of material to aid the slipping of clothing upon the arms and legs of the users.

SUMMARY OF THE INVENTION

The general purpose of the present invention, which will be described subsequently in greater detail, is to provide a new prosthesis dressing aid which has many of the advantages of the prosthesis dressing aids mentioned heretofore and many novel features that result in a new prosthesis dressing aid which is not anticipated, rendered obvious, suggested, or even implied by any of the prior art prosthesis dressing aids, either alone or in any combination thereof. The present invention includes a prosthesis being adapted to be attached to a user's limb; and also includes a sleeve being removably disposed about the prosthesis to facilitating dressing of the prosthesis with an article of clothing. None of the prior art includes the combination of the elements of the present invention.

There has thus been outlined, rather broadly, the more important features of the prosthesis dressing aid in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new prosthesis dressing aid which has many of the advantages of the prosthesis dressing aids mentioned heretofore and many novel features that result in a new prosthesis dressing aid which is not anticipated, rendered obvious, suggested, or even implied by any of the prior art prosthesis dressing aids, either alone or in any combination thereof.

Still another object of the present invention is to provide a new prosthesis dressing aid for allowing a user to easily slip an article of clothing about the artificial limb.

Still yet another object of the present invention is to provide a new prosthesis dressing aid that is easy and convenient to use.

Even still another object of the present invention is to provide a new prosthesis dressing aid that prevents the article of clothing from getting hung up on the prosthesis as the user attempts to dress oneself.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an exploded perspective view of the sleeve of the present invention.

FIG. 4 is a perspective view of the lower portion of the sleeve of the present invention.

DESCRIPTION OF THE PREFERRED EMBODIMENT

Figure 1:
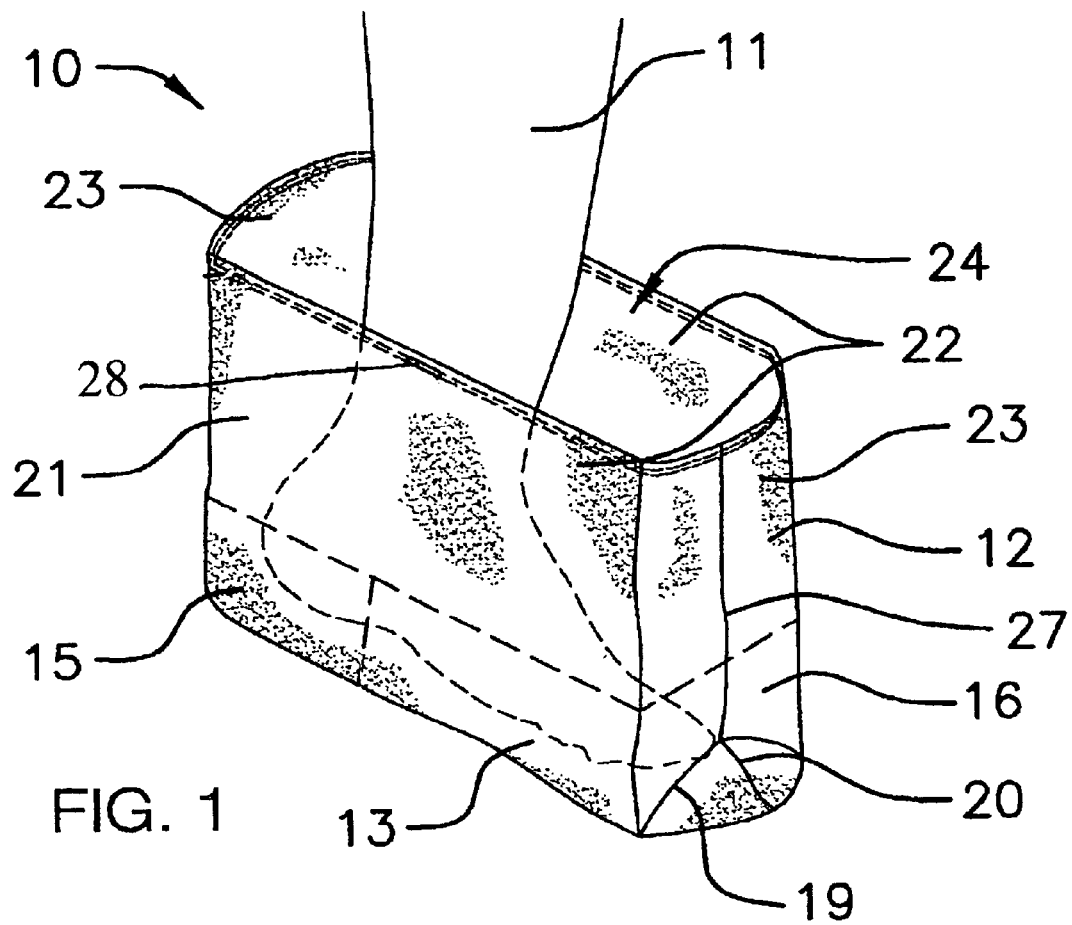
FIG. 1 is a perspective view of a new prosthesis dressing aid according to the present invention.
Figure 2:
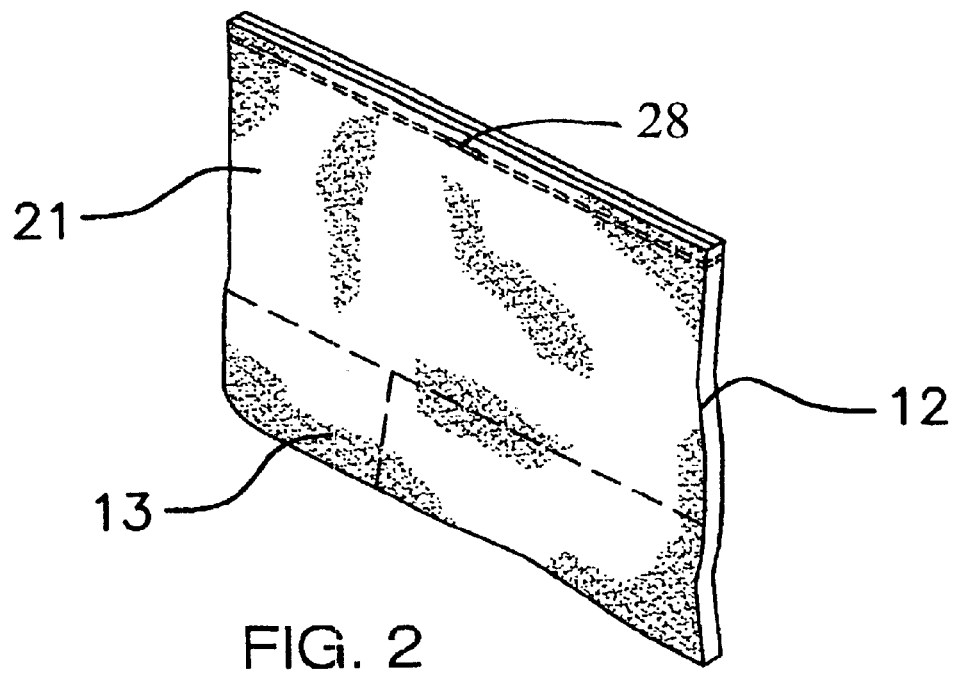
FIG. 2 is a perspective view of the sleeve of the present invention.

With reference now to the drawings, and in particular to FIGS. 1 through 4 thereof, a new prosthesis dressing aid embodying the principles and concepts of the present invention and generally designated by the reference numeral 10 will be described.

As best illustrated in FIGS. 1 through 4, the prosthesis dressing aid 10 generally comprises a prosthesis 11 being adapted to be attached to a user's limb with the prosthesis 11 being an artificial limb.

A sleeve 12 is removably disposed about the prosthesis 11 to facilitate the dressing of the prosthesis 11 with an article of clothing. The sleeve 12 has a lower member 13 having side and end walls 15,16 and open top and bottom end 14,17, and also has an upper member 21 having side and end walls 22,23, and also having open top and bottom ends 24,25 with bottom edges 26 of the side and end walls 22,23 of the upper member 21 being detachably and conventionally attached to top edges 18 of the side and end walls 15,16 of the lower member 13. The sleeve 12 also has a means of securing the sleeve 12 about the prosthesis 11. Each of the end walls 16 of the lower member 13 has an arc-shaped crease 19 extending from one bottom corner to another bottom corner thereof, and also has a longitudinal crease 20 being centrally disposed in the end wall 16 and extending from the open bottom end 14 to the open top end 17 thereof to facilitate slipping the sleeve 12 about the prosthesis 11. Each of the end walls 23 of the upper member 21 has a longitudinal crease 27 being centrally disposed therein and extending from the open bottom end 25 to the open top end 24 to facilitate slipping the sleeve 12 about the prosthesis 11. The assembly of securing the sleeve 12 about the prosthesis 11 includes a drawstring 28 being conventionally attached to the side and end walls 22,23 of the upper member 21. The drawstring 28 is generally disposed in the side and end walls 22,23 near the open top end 24 of the upper member 21.

In use, the user extends the prosthesis 11 in the sleeve 12 through the open top end 24 of the upper member 21, and secures the sleeve 12 about the prosthesis 11 using the handle members 28, and then dresses an article of clothing about the sleeve 12 and the prosthesis 11, and detaches upper member 21 of the sleeve 12 from the lower member 13 and removes the upper and lower members 13,21 of the sleeve 12 from about the prosthesis 11.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the prosthesis dressing aid. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A prosthesis dressing aid comprising:

a prosthesis being adapted to be attached to a user's limb, said prosthesis being an artificial limb;

a sleeve being removably disposed about said prosthesis to facilitate the dressing of said prosthesis with an article of clothing, said sleeves having a lower member having side and end walls and open top and bottom ends, and also having an upper member having side and end walls, and also having open top and bottom ends with bottom edges of said side and end walls of said upper member being detachably attached to top edges of said side and end walls of said lower member;

said sleeve also having a means of securing said sleeve about said prosthesis.

2. The prosthesis dressing aid as described in claim 1, wherein each of said end walls of said lower member has an arc-shaped crease extending from one bottom corner to another bottom corner thereof, and also has a longitudinal crease being centrally disposed in said end wall and extending from said open bottom end to said open top end thereof to facilitate slipping said sleeve about said prosthesis.

3. The prosthesis dressing aid as described in claim 2, wherein each of said end walls of said upper member has a longitudinal crease being centrally disposed therein and extending from said open bottom end to said open top end to facilitate slipping said sleeve about said prosthesis.

4. The prosthesis dressing aid as described in claim 3, wherein said means of securing aid sleeve about said prosthesis includes a drawstring being attached to said side and end walls of said upper member.

5. The prosthesis dressing aid as described in claim 4, wherein said drawstring is generally disposed in said side and end walls near said open top end of said upper member.

6. A method of using a prosthesis dressing aid comprising the steps of:

providing a prosthesis being adapted to be attached to a user's limb, and also providing a sleeve being removably disposed about said prosthesis to facilitating dressing of said prosthesis with an article of clothing, said sleeve having a lower member having side and end walls and open top and bottom ends, and also having an upper member having side and end walls, and also having open top and bottom ends with bottom edges of said side and end walls of said upper member being detachably attached to top edges of said side and end walls of said lower member, said sleeve also having a means of securing said sleeve about said prosthesis;

extending said prosthesis in said sleeve through said open top end of said upper member;

securing said sleeve about said prosthesis;

dressing an article of clothing about said sleeve and said prosthesis; and detaching said upper member of said sleeve from said lower member and removing said upper and lower members of said sleeve from about said prosthesis.

* * * * *